US006623697B2

United States Patent
Fuerst et al.

(10) Patent No.: US 6,623,697 B2
(45) Date of Patent: Sep. 23, 2003

(54) ANALYSIS DEVICE FOR ANALYZING SAMPLES

(75) Inventors: Otto Fuerst, Viernheim (DE); Paul Jansen, Mannheim (DE); Thomas Jaeck, Heddesheim (DE)

(73) Assignee: Roche Diagnostics GmbH, Manheim (DE)

( * ) Notice: Subject to any disclaimer, the term of this patent is extended or adjusted under 35 U.S.C. 154(b) by 282 days.

(21) Appl. No.: 09/766,509

(22) Filed: Jan. 19, 2001

(65) Prior Publication Data

US 2001/0026772 A1 Oct. 4, 2001

(30) Foreign Application Priority Data

Jan. 21, 2000 (DE) .......................... 100 02 475

(51) Int. Cl.[7] .................. G01N 21/00; G01N 31/00; G01N 33/00; G01N 1/10; G01N 35/02; E03B 11/00
(52) U.S. Cl. .............................. 422/64; 422/73; 422/63; 422/100; 436/180; 436/49; 137/266; 137/263
(58) Field of Search .......................... 422/100, 64, 73, 422/63; 436/180, 49; 137/263, 266

(56) References Cited

U.S. PATENT DOCUMENTS

| 5,309,775 | A |   | 5/1994  | Andersen et al.          |
|-----------|---|---|---------|--------------------------|
| 5,610,069 | A | * | 3/1997  | Clark et al. ..... 436/49 |
| 5,679,575 | A | * | 10/1997 | Kubota et al. .... 436/49 |
| 5,807,523 | A | * | 9/1998  | Watts et al. ..... 422/64 |
| 5,820,824 | A |   | 10/1998 | Tanaka ........... 422/100 |
| 5,832,948 | A | * | 11/1998 | Schell ............ 137/93 |
| 5,885,530 | A | * | 3/1999  | Babson et al. ... 422/65 |
| 5,902,548 | A | * | 5/1999  | Watts et al. ..... 422/63 |
| 5,939,330 | A | * | 8/1999  | Peterson ......... 436/180 |
| 5,940,178 | A | * | 8/1999  | Barber et al. ... 356/339 |
| 5,948,359 | A | * | 9/1999  | Kalra et al. ..... 422/65 |
| 6,027,691 | A | * | 2/2000  | Watts et al. ..... 422/64 |
| 6,133,045 | A | * | 10/2000 | Johnson et al. .. 436/177 |
| 6,213,139 | B1 | * | 4/2001 | Rogers ............ 137/1  |
| 6,349,264 | B1 | * | 2/2002 | Rhett et al. ..... 702/19 |

FOREIGN PATENT DOCUMENTS

| EP | 0 645 631 A2 | 3/1995 |           |
|----|--------------|--------|-----------|
| EP | 0825446 A2   | 2/1998 | G01N/35/10 |
| EP | 0918221 A2   | 5/1999 | G01N/35/02 |
| WO | WO 97/35173  | 9/1997 |           |

* cited by examiner

Primary Examiner—Jill Warden
Assistant Examiner—Brian R. Gordon
(74) Attorney, Agent, or Firm—Woodard, Emhardt, Moriarty McNett & Henry LLP

(57) ABSTRACT

Analysis device for analyzing samples, in particular of body liquids, with respect to components contained therein. It comprises a plurality of liquid handling (LH) stations. At at least a part of the LH stations there is a production of liquid waste whereby said LH-station form liquid waste sources. The liquid waste is evacuated, with at least one pump, from the liquid waste sources, with different proportions of air, via a liquid waste conducting system, into a liquid waste container.

Figure 1:
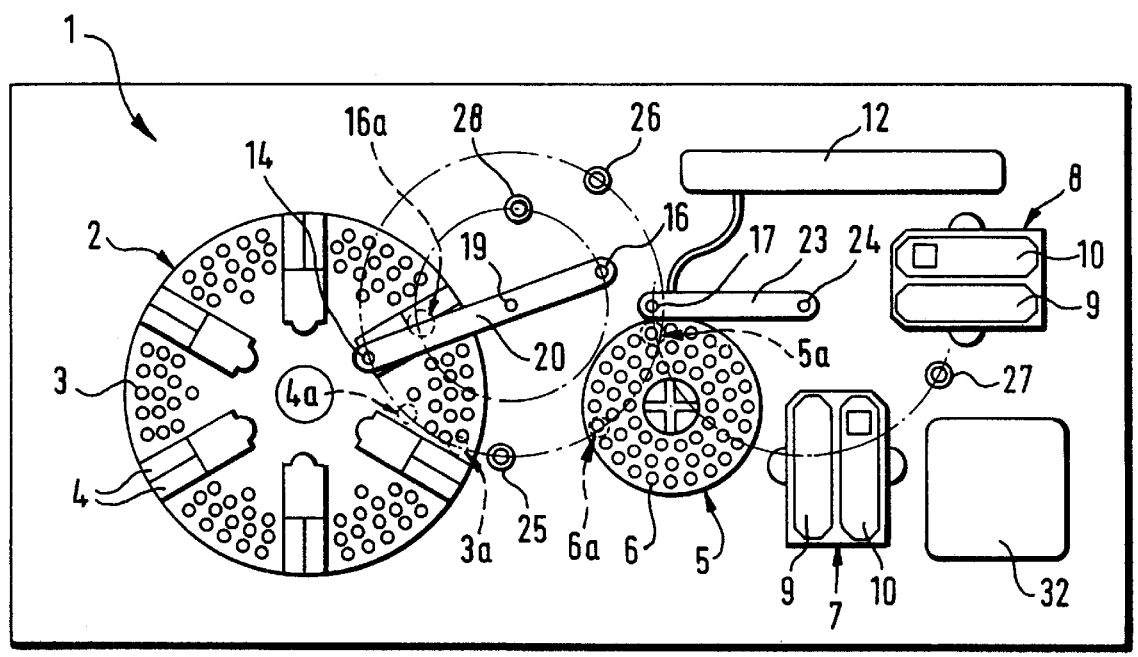

A substantial reduction of foam production is obtained by connecting at least two liquid waste sources to the liquid waste container via at least two liquid waste lines leading separately into the liquid waste container, whereas liquid waste sources with a higher average air proportion are connected to a first liquid waste line and liquid waste sources with a lower average air proportion are connected to a second liquid waste line.

9 Claims, 2 Drawing Sheets

ANALYSIS DEVICE FOR ANALYZING SAMPLES

The invention relates to an analysis device for analyzing samples, in particular for medical applications. The samples are preferably body liquids, as e.g. blood or urine. The target of the analysis is to detect the existence, or the concentration, respectively, of a component (analyte) of the sample.

In such analysis devices, the procedures necessary for the analysis are performed automatically. To this end, samples and reagent components are dosed into containers (reaction vessels), mixed and incubated for determined reaction times. The reaction of the sample with the reagents leads to a measurable change which is characteristic for the analysis, and is measured and evaluated for the determination of the analysis result. Numerous different analysis devices are known. These differ widely with respect to reaction principles (e.g. classical clinical chemistry; chemoimmunology, DNA analytics), and with respect to the measured variable characteristic for the analysis (e.g. photochemically measurable color changes, turbidimetry, electrochemical measurement) as well as with respect to the design of the apparatus. These different methods are known and are not the subject of the present invention.

Many analysis devices have in common that they comprise a plurality of (stationary or movable) stations, where partial steps of the procedure necessary for the analysis are performed. Most of these stations serve, in any form, for handling liquids; thus, they are generally designated liquid handling (LH) stations. Typical examples are dosing stations, where a liquid (reagent or sample) is dosed into a reaction vessel by means of thin tubes (dosing needles), or mixing stations, where liquids are mixed with other liquids and/or solid components (e.g. suspended pellets as carriers for fixed immune reagents, so-called beads) by means of a stirrer immerged into the reaction vessel. Measurement stations, too, can be regarded as LH stations, as far as the measurement requires a liquid handling step, as e.g. the filling and emptying of a measuring cell.

The LH stations of such analysis devices typically include one or more washing stations, where a processing tool, e.g. a dosing needle or a stirrer, is cleaned. A very good cleaning of the tools which are submerged into liquids of different composition, is very important with respect to the exactness of the analysis, as impurities lead to a transfer of one liquid to another (passive dispersal). In order to obtain a cleaning as effective as possible, different designs of washing stations were proposed. An example of washing stations which can be applied very advantageously with the present invention, is described in international patent application WO 97/35173.

At a part of the LH stations of common analysis devices there is a production of liquid waste which must be disposed of. In case of washing stations, the liquid waste consists, in particular, of the washing liquids used there, with the washed-off residues of reagents and/or samples. At other LH stations there may be produced liquid waste, too, e.g. a reaction mixture at the measuring station which is not needed any longer after the termination of the measurement. At other processing stations, e.g., dosing surpluses may be produced, being evacuated at an overflow of the reaction vessel. All LH stations producing liquid waste are designated here as liquid waste sources.

Typically, the liquid waste is disposed of by guiding it into a liquid waste container via a conducting system. For some analysis devices, the liquid waste container is arranged in such a way below the liquid waste sources, that the liquid waste drains by gravity only. However, this requires a relatively high design shape of the device as well as liquid waste tubes with large diameter and sufficient gradient. Furthermore, the washing stations of such devices must be designed in a way that the washing liquid drains spontaneously. In order to avoid these problems, pumps are used which evacuate the liquid waste at the liquid waste sources and transport it to the liquid waste container.

Generally, the liquid waste produced at the liquid waste sources of analysis devices does not only consist of liquids, but contains portions of air, which vary with respect to their quantity during the procedure performed by the analysis device. Thus, the term "liquid waste" must be understood in a way that this is a kind of waste which can be pumped as a liquid, but may, apart from the liquid components, contain air (or other gases) as well as dispersed solid matter. As far as the liquid portion of the waste is referred to here, this is the average volume ratio of liquid in the tubes leading from the corresponding liquid waste source to the liquid waste container, during the processing of the device.

The liquid waste of analysis devices usually contains components (in particular detergents contained in washing liquids and in reagents) which produce foam in the liquid waste container. This leads to severe disadvantages. The foam rapidly fills the liquid waste container, making it necessary to empty it in order to avoid contamination. Furthermore, the foam interferes with the liquid level detection most liquid waste containers are equipped with.

For decreasing the foam production in the liquid waste container, it is possible to add chemical substances (antifoam) to the liquid waste, which impede the foam production. However, this requires additional handling steps and/or special constructive measures on the device for the dosing of antifoam compounds. Furthermore, the chemical foam elimination causes additional cost and, possibly, additional problems with the environmentally appropriate disposal if the liquid waste from the liquid waste container.

Another possibility for reducing the problems caused by foam production is the use of particularly big liquid waste containers. However, this is contrary to the required space-saving design of analysis devices.

On this basis, the invention addresses the problem to reduce the foam production in the liquid waste containers of analysis devices with as little expense as possible, with respect to the design of the device as well as with respect to the handling of the device.

This problem is solved by an analysis device for analyzing samples, in particular body liquids, with respect to components contained therein, with a plurality of liquid handling (LH) stations, which include processing stations. At these processing stations, processing steps are performed by means of processing tools as e.g. a dosing needle or a stirrer, at liquids contained in containers. At at least a part of the LH station, liquid waste is produced, thus forming liquid waste sources. The liquid waste produced there, containing different portions of air, is evacuated by means of at least one pump, from the liquid waste sources, via a liquid waste conducting system, to a liquid waste container. The liquid waste conducting system has at least two separate tubes leading into the liquid waste container; a plurality of liquid waste sources is connected to at least one of these tubes. From these sources, there are separate tubes acting as secondary lines and guiding towards a line junction. From this line junction, a common tube leads as primary line into the liquid waste container. The secondary lines are grouped together in such a way that in one of the at least two lines guiding into the liquid waste container, there is liquid waste with a higher portion of air, and in another of the at least two lines guiding into the liquid waste container, there is liquid waste with a lower portion of air.

Analysis devices with conducting systems which comprise a plurality of separate liquid waste lines conducted to the liquid waste container, are known in different designs, e.g. from U.S. Pat. No. 5,820,824, EP 0825446 A2 and EP 0918221 A2.

In the scope of this invention it was determined that the foam production can be reduced dramatically by combining the liquid waste flow from the different liquid waste sources depending on the average amount of air transported in the tubes of the liquid waste conducting system, so that at least two partial flows are guided through separate lines and are pumped completely separate into the liquid waste container, whereas one of these partial flows contains a relatively high air proportion and the other partial flow contains a relatively low air proportion.

The liquid waste sources are grouped in a way that a plurality of liquid waste sources are connected to at least one of the separate lines leading into the liquid waste container. For this purpose, separate tube sections ("secondary lines") exist, leading from the liquid waste sources to at least one line junction. After the junction of all partial flows of a group, the resulting liquid waste flows, in a common line section ("primary line" of the group) to the liquid waste container. According to the number of liquid waste sources, different combinations are possible.

The liquid waste source groups, the wastes of which are grouped and commonly lead to the liquid waste container, are divided in a way that the resulting liquid proportions of the two lines leading into the liquid waste container, significantly differ from each other (preferably at least by the factor 1,5). Preferably, there is a first group consisting of liquid waste source with a relatively high air proportion, and a second group consisting of liquid waste sources with a relatively low air proportion. "Relatively high" and "relatively low" has to be understood in a way that in the group with the higher air proportion there is no liquid waste source with a lower air proportion than the highest air proportion of the other group. With other words, there is a limit value for the average air proportion in a way that the liquid waste sources of the first group are above, and the liquid waste sources of the second group are below this limit value.

However, the designation "relatively low air proportion" must not be understood in a way that the air volume flow is lower than the water volume flow. Due to the design is and the operation of common LH stations, and, in particular, common washing stations, even for a liquid waste source with "relatively low" air proportion, during the major part of the overall operating time, only or preponderantly air is evacuated from the liquid waste source. In the scope of the experimental evaluation of the invention, even liquid waste sources with an average air volume proportion of more than 80% (e.g. an average of 5 seconds of liquid transport per minute) were assigned to the group with a "relatively low" air proportion.

A high air volume flow, as compared to the water volume flow, results, in particular, in analysis devices where the liquid waste of a plurality of liquid waste sources is evacuated with a common, continuously driven pump. The application of a common pump results in substantial savings of cost, constructive volume and weight, as compared to individually controlled evacuation pumps assigned to separated liquid waste sources. On the other hand, these designs have particular problems with foam production.

If there are four or more liquid waste sources, it is in principle possible to lead more than two primary lines to the liquid waste container. According to the experimental evaluation of the invention, this is not necessary in the normal case. It is enough to have two separate liquid waste lines, differing as described with respect to the transported air proportion, leading into the liquid waste container.

Figure 3:
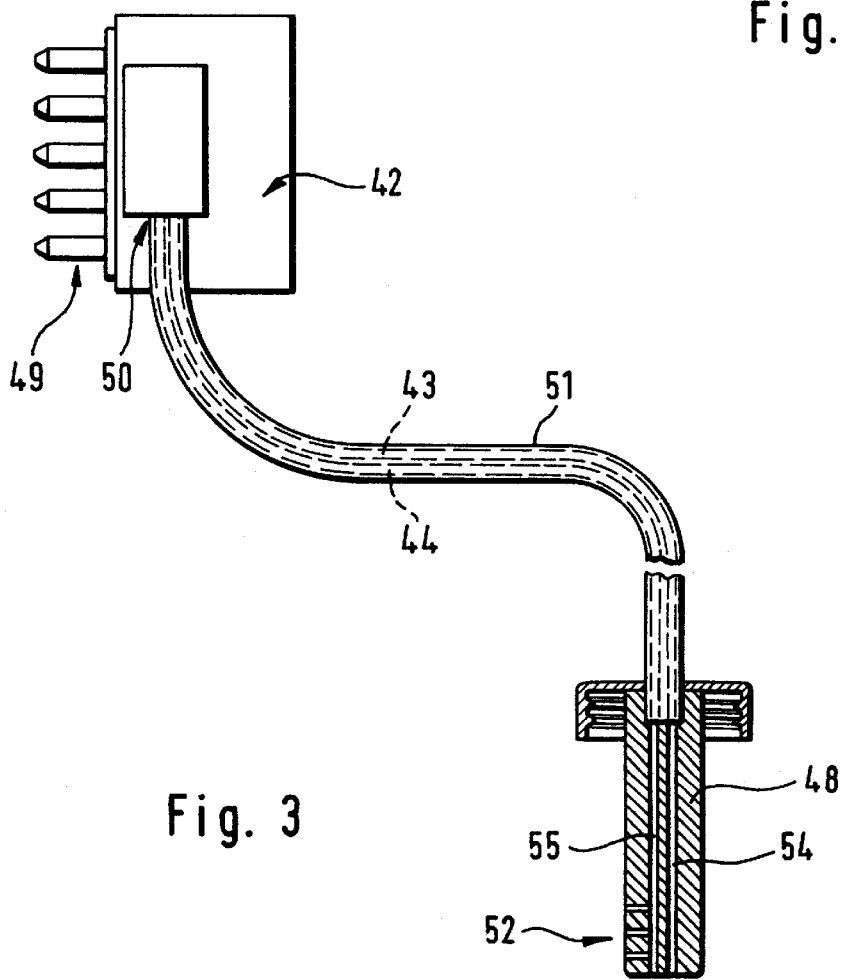
Figure 2:
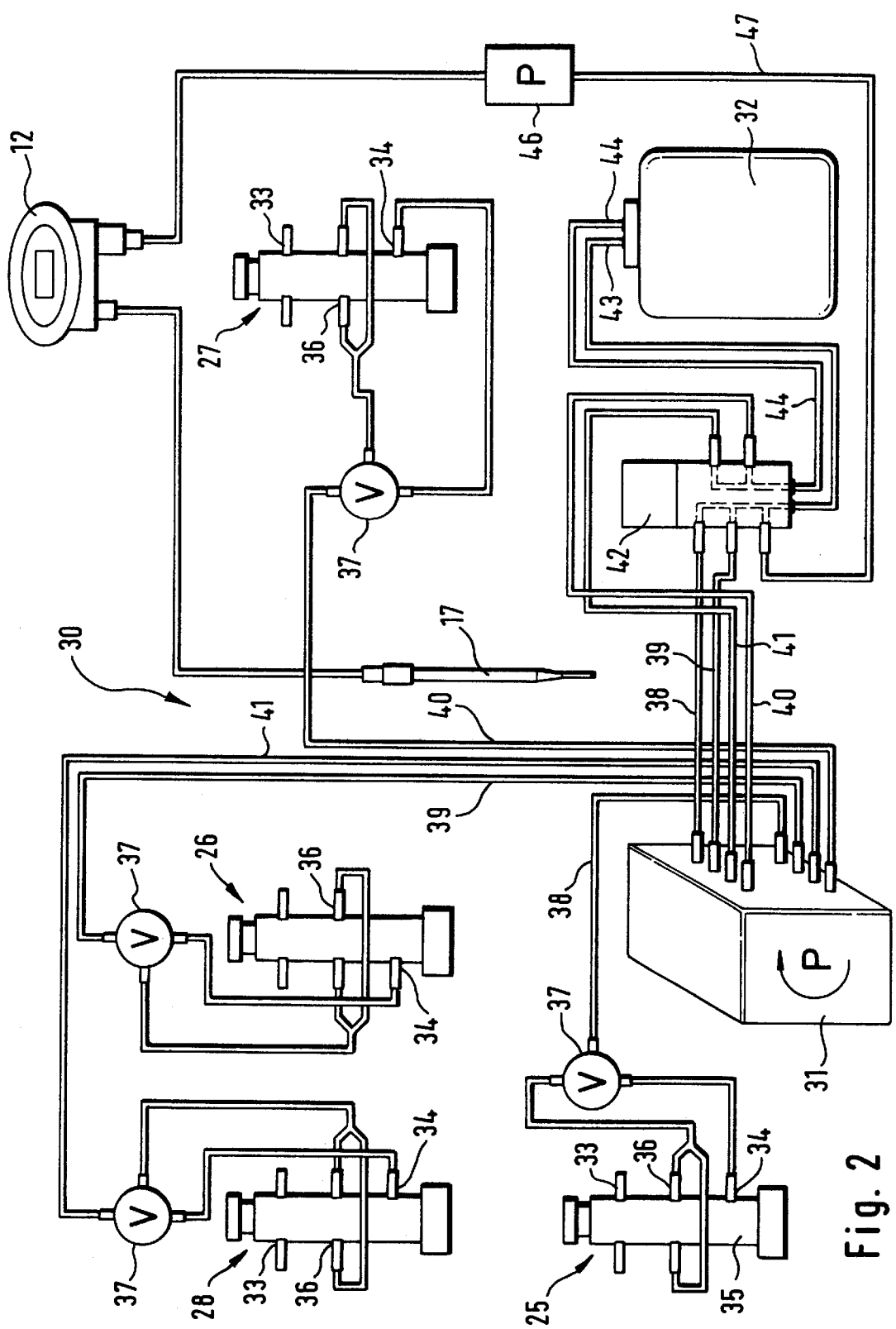

The invention will subsequently be explained in detail on the basis of an example represented in the figures. In order to obtain preferred embodiments of the invention, the features and characteristics represented can be applied individually or in a combination. The figures show:

FIG. 1 a schematic top view onto an analysis device,

FIG. 2 a conducting system diagram of the part of the analysis device which is essential for this invention, FIG. 3 a lateral view, partially as a sectional view, of the constructive parts used for the section of the liquid waste conducting system, between a line junction and the liquid waste container.

FIG. 1 schematically shows the essential processing stations of an analysis device appropriate for immunochemical analyses with ECL (electrochemical luminescence) detection. These include a sample reagent rotor with sample containers 3 and reagent containers 4, an incubation rotor 5 with reaction vessels 6 arranged in a plurality of lines, two stations 7 and 8 with auxiliary liquids for bead processing (one being a rinsing liquid in rinsing liquid containers 9 as transport, cleaning and reaction medium for the beads as well as for conditioning the ECL measuring cell before the measurement, and a second one being a cleaning liquid in the cleaning containers 10 for cleaning the ECL measuring cell after the measurement).

For analyzing the samples in the sample containers 3, the sample liquids and the reagents (including beads) are taken from the containers 3 and 4 at the processing stations 3a or 4a, respectively, of the sample reagent rotor 2, transferred to the reaction vessels 6 located in the processing stations 6a of the incubation rotor 5, and mixed there. After the end of the reaction, the resulting reaction mixture is evacuated from the reaction vessels 6 located in the processing station 5a into a measuring chamber 12, where a signal, characteristic for the analysis, is measured (namely an ECL signal).

The analysis device 1 comprises processing tools for the performance of these reaction steps. These include, in the presented case, a dosing needle 14, a stirrer 16 and a suction needle 17. The processing tools are movable around swivel arms 20, 23 in horizontal and in vertical direction (around a swivel axis 19 or 24, respectively). The needles 14 and 17 as well as the stirrers 16 extend downwards from the swivel arms 20, 21 in vertical direction; thus, they can only be recognized as dots in FIG. 1. For the device represented, the stirrer 16 is used to homogenize reagent liquids containing beads, located in a reagent container 4 at a processing station 16a on the sample reagent rotor 2.

For cleaning the processing tools, corresponding washing stations are provided; namely two dose needle washing stations 25 and 26, a suction needle washing station 27 and a stirrer washing station 28.

Details of the function of the analysis device are not significant for the present invention and can be taken from relevant publications. For the invention it is important that the analysis device 1 has a plurality of LH stations where liquid waste is produced, thus forming the liquid waste sources. In the represented case, these are mainly the washing stations 25–28. The liquid waste of these is evacuated via a liquid waste conducting system (represented in FIG. 2 and designated in its entirety with 30) and via a pump 31, into a liquid waste container 32. A further liquid waste source is the measuring chamber 12, also connected to the conducting system 30.

Each of the washing stations 25–28 has two evacuation points, namely a first evacuation point 34, which is located at the bottom of the respective washing liquid container 35, and a second evacuation point for evacuating washing liquid at an overflow of the washing liquid container 35. In the represented design, the second evacuation point 36 is realized by a plurality of evacuation connections having their openings at the same level of the washing liquid container. Further information about the construction and the function of such washing stations can be gathered from WO 97/35173.

The evacuation points 34, 36, respectively, can be connected alternately, via a switch valve 37, with a line section (secondary line) 38–41 which is common for the evacuation points 34, 36, but separate for the different washing stations 25–28 and leads from the washing stations via the pump 31 to a line junction 42.

The pump 31 is a multichannel type, i.e. it is able to pump liquid into a plurality of different lines by means of one common pump drive. In case of the represented, preferred design, it is located in the secondary lines 38–41. However, it may also be located at another position in the liquid waste conducting system 30. A multichannel pump is generally preferred which pumps liquid waste through a plurality of lines with one common pump drive. A multichannel hose pump is particularly appropriate.

If pump 31 is operating, it evacuates the liquid waste from all connected liquid waste sources simultaneously (in the represented case, from all washing stations 25–28). However, the liquid volumes produced there, are different. The dosing needle washing stations 25 and 26 generate a liquid waste with a relatively high liquid proportion, as the dosing needles are used for the transfer of different liquids during the analysis process, and thus must be cleaned several times during each analysis. During each cleaning process, washing liquid is pumped into the washing stations via the washing liquid connections 33, in order to clean the outside of the dosing needles. Further liquid waste components are generated by rinsing the inside of the dosing needle. These liquid waste components are evacuated via the evacuation points 34 or 35, according to the switching position of the switch valve 37. If the switch valve is set in a way that the pump 31 is connected to the evacuation points 36 at the overflow of the washing liquid container 35, mainly air is evacuated.

The suction needle washing station 27 and the stirrer washing station 28 are used less frequently, as the prepared reaction liquid must be evacuated only once for an analysis, and as the cleaning of the stirrer is only necessary with long timely intervals, depending on the test procedure. Thus the washing stations 27 and 28 are only during a very small proportion of the operating time of the pump 31 in a state of essential liquid evacuation. During the by far major part of its operating time, the pump 31 only evacuates air from these liquid waste sources.

At the junction 42, the liquid waste from the washing stations is grouped in a way that the liquid waste from the liquid waste sources with a higher air proportion, namely from the suction needle washing station 27 and the stirrer washing station 28, flows into the liquid waste container via a first primary line 44, and the liquid waste from the liquid waste sources with a lower air proportion, namely the dosing needle washing stations, 25 and 26, flows, via a second primary line 43, separated from the first primary line 44, into the liquid waste container 32. Accordingly, the secondary lines 38 and 39 are connected to the primary line 43, and the secondary lines 40 and 41 are connected to the primary line 44. As a whole, the liquid waste conducting system is designed in a way that two pairs each of the four liquid waste lines leading from the washing stations 25–28 to the liquid waste container 32, are completely separated, namely, on one hand, the liquid waste lines of the washing stations 25, 26, with a lower air proportion, consisting of the secondary lines 38 and 39 and the primary line 43, and, on the other hand, the liquid waste lines of the washing stations 27, 28, with a higher air proportion, consisting of the secondary lines 40 and 41 and the primary line 44.

A further liquid waste source is formed by the measuring cell 12. Measuring liquid pumped from the measuring cell 12 by means of the measuring liquid pump 46, flows to the line junction 42 via a further secondary line 47, and from there to the liquid waste container 32. As this liquid waste almost completely consists of liquid, the secondary line 47 is connected to the primary line 43, transporting the liquid waste with the lower air proportion.

FIG. 3 shows a preferred embodiment of the line junction 42, the downstream line section with the primary lines 43 and 44, as well as a connection piece 48 for the connection to the liquid waste container 32.

Conveniently, the line junction is formed by unitary element, having a number of inlet connections 49, corresponding to the number of secondary lines 38 to 41, 47. The number of outlet connections 50 corresponds to the number of primary lines 43, 44, leading to the connection piece 48 and thus to the container 32. Instead of the represented one-piece design, other designs may be used for the line junction 42, e.g. consisting of a plurality of common hose connection elements (Y-branches, T-branches).

The primary lines 43, 44 of the line system 30 are preferably combined in a multichannel hose 51, which may include, in addition to the chambers for the primary lines 43 and 44, al least one more chamber, not represented in the figure, containing electrical lines, in particular for the liquid level detection in the liquid waste container 32.

At the lower end of the represented connection piece 48, a sensor 52 with bores for the level detection is provided. With respect to a low foam production, it has proven advantageously if the primary lines 43 and 44 debouch into the liquid waste container in essentially parallel direction and with only a small distance from each other (preferably max. 1 cm). Accordingly, the connection piece 48 has two parallel bores 54 and 55, with a small distance from each other, forming the last section of the primary lines 43, 44.

What is claimed is:

1. In an analysis device for analyzing samples comprising a plurality of liquid handling (LH) stations which include processing stations, including at least one of a detection station, a dispensing station, washing station, and mixing station and wherein processing steps are performed to sample liquids contained in containers with processing tools including at least one of a dosing needle and a stirrer, and wherein liquid waste is produced at least at a part of the liquid handling stations, the improvement comprising:

a liquid waste conduction system comprising:

a plurality of liquid waste sources associated with said processing stations each of said liquid waste sources including different proportion of air;

a liquid waste container;

at least first and second primary waste lines leading to the liquid waste container;

a plurality of separate secondary waste lines leading from each of said plurality of liquid waste sources;

a line junction connecting at least one of said secondary waste lines with the first primary waste line and at least a second of said secondary waste lines with the second primary waste line;

at least one evacuation pump for transferring liquid waste from said liquid waste sources to said liquid waste container; and wherein the first primary waste lines transports liquid waste with a higher proportion of air and the second primary waste line transports liquid waste with a lower air proportion.

2. The analysis device according to claim 1, wherein the at least one evacuation pump for transferring liquid waste from said liquid waste sources to said liquid waste container is a common multichannel pump.

3. The analysis device according to claim 2, wherein the multichannel pump is continuously driven.

4. The analysis device according to claim 2, wherein the pump is located in the secondary lines upstream form the line junction.

5. The analysis device according to claim 1, wherein the at least one of the liquid waste sources is a washing station for cleaning a processing tool by means of a washing liquid.

6. The analysis device according to claim 5, wherein the plurality of liquid waste sources include at least two washing stations and said washing stations are connected to at least one of said first and second primary waste lines via said secondary lines and said line junction.

7. The analysis device according to claim 5, wherein at least one washing station comprises a washing liquid container with a first evacuation point at the bottom of the washing liquid container and a second evacuation point at an overflow of the washing container.

8. The analysis device according to claim 7, wherein the first evacuation point and the second evacuation point are connected to a switch valve.

9. The analysis device according to claim 1, wherein the exit openings of the separate lines leading into the liquid waste container are arranged at most 1 cm from each other.

* * * * *

UNITED STATES PATENT AND TRADEMARK OFFICE
CERTIFICATE OF CORRECTION

PATENT NO. : 6,623,697 B2
DATED : September 23, 2003
INVENTOR(S) : Fuerst et al.

It is certified that error appears in the above-identified patent and that said Letters Patent is hereby corrected as shown below:

<u>Title page,</u>
Item [73], please amend the name of the Assignee to read -- Roche Diagnostics Corporation, Indianapolis, IN (US) --.

Signed and Sealed this

Sixth Day of January, 2004

JAMES E. ROGAN
*Director of the United States Patent and Trademark Office*